United States Patent [19]

Giral et al.

[11] Patent Number: 4,663,329
[45] Date of Patent: May 5, 1987

[54] THIENOPYRIDINONE DERIVATIVES AND ANTI-BACTERIAL COMPOSITIONS CONTAINING THEM

[75] Inventors: Louis Giral, Montpellier; Marc Puygrenier, Bry-sur-Marnes; Jacques Bompart, Castries, all of France

[73] Assignee: Sanofi, Paris, France

[21] Appl. No.: 730,184

[22] Filed: May 3, 1985

[30] Foreign Application Priority Data

May 4, 1984 [FR] France .............................. 84 06970

[51] Int. Cl.⁴ ..................... A61K 31/44; C07D 495/04
[52] U.S. Cl. .................................... 514/301; 514/231; 514/255; 544/127; 544/362; 546/114; 549/68
[58] Field of Search ................ 546/114; 544/127, 362; 514/231, 255, 301

[56] References Cited

U.S. PATENT DOCUMENTS 3,951,989  4/1976  Kuwada et al. ................... 546/114
4,195,087  3/1980  Simonovitch, II ................. 546/123

FOREIGN PATENT DOCUMENTS 858479  1/1978  Belgium .
2373542  7/1978  France .

Primary Examiner—Henry R. Jiles
Assistant Examiner—Bernard I. Dentz
Attorney, Agent, or Firm—Bacon & Thomas

[57] ABSTRACT

Thienopyridinone derivatives of the general formula:

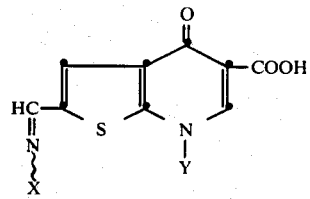

in which Y represents hydrogen or a lower alkyl group and X represents:
a hydroxy, lower alkanoyloxy, lower alkoxy unsubstituted or substituted by a hydroxy, lower alkoxy, di-(lower alkyl)-amino, piperidino, pyrrolidino, morpholino or N-(lower alkyl)-piperazino group, a group of formula:

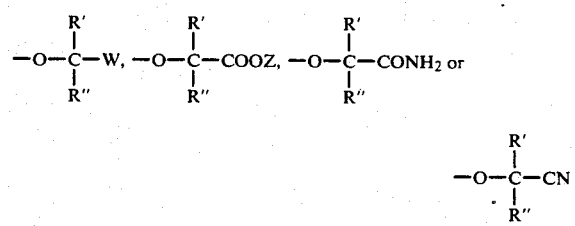

in which R' and R", which are the same or different, each represent hydrogen or a lower alkyl, W represents hydrogen or a lower alkyl radical or a vinyl or ethynyl group and Z represents hydrogen or a lower alkyl radical,
a phenyl radical unsubstituted or substituted by an atom of fluorine, chlorine, bromine or iodine or by a hydroxy, lower alkoxy or nitro group,
a group of formula:

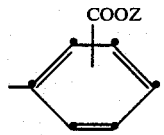

in which Z has the same meaning as above,
an amino, lower alkylamino or —NHCOOZ group in which Z has the same meaning as above and pharmaceutically acceptable salts thereof.

They possess antibacterial properties.

12 Claims, No Drawings

THIENOPYRIDINONE DERIVATIVES AND ANTI-BACTERIAL COMPOSITIONS CONTAINING THEM

The present invention relates to novel thienopyridinone derivatives having antibacterial activity, to their process of preparation and to pharmaceutical compositions containing them as active principles.

In particular, the invention relates to thienopyridinone derivatives of general formula:

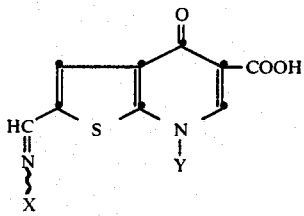

in which Y represents hydrogen or a lower alkyl group and X represents:
a hydroxy, lower alkanoyloxy, lower alkoxy unsubstituted or substituted by a hydroxy, lower alkoxy, di-(lower alkyl)-amino, piperidino, pyrrolidino, morpholino or N-(lower alkyl)-piperazino group, a group of formula:

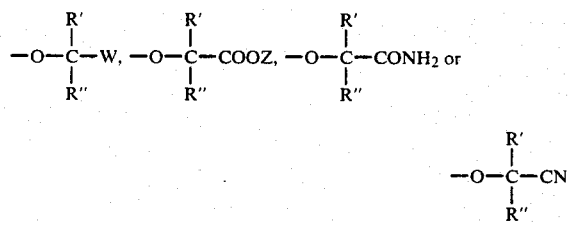

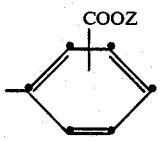

in which R' and R", which are the same or different, each represent hydrogen or a lower alkyl, W represents hydrogen or a lower alkyl radical or a vinyl or ethynyl group and Z represents hydrogen or a lower alkyl radical,
a phenyl radical unsubstituted or substituted by an atom of fluorine, chlorine, bromine or iodine or by a hydroxy, lower alkoxy or nitro group, a group of formula:

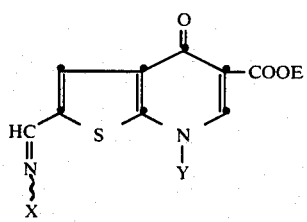

in which Z has the same meaning as above,
an amino, lower alkylamino or —NHCOOZ group in which Z has the same meaning as above.
"Lower alkyl" as used in the present context means saturated aliphatic hydrocarbon groups having up to 4 carbon atoms.

The terms "lower alkanoyloxy" and "lower alkoxy" represent carbonyloxy or hydroxy groups respectively, these groups being substituted by lower alkyl groups such as hereabove defined.

In view of the —CH=N— X groups, the compounds of formula I can exist in the form of syn- or anti-isomers. These isomers when taken individually or in the form of mixtures are also included within the present invention.

Similarly, the invention relates to pharmaceutically acceptable salts of the compounds of formula I.

These pharmaceutically acceptable salts are particularly referred to as alkali metal salts such as lithium, sodium or potassium salts, the alkaline earth metal salts such as calcium or magnesium salts or the ammonium salts such as those obtained from ammonia or an amine such as methylamine, ethylamine, dimethylamine, diethylamine, triethylamine, ethanolamine, diethanolamine, trometamol and the like.

The compounds of the invention have been found to possess valuable antibacterial properties likely to render them useful in the treatment of diseases provoked by the growth of pathogenic bacteria.

In accordance with another aspect of the invention, there is provided a process for preparing the compounds of formula I above in which X has the same meaning as above defined and pharmaceutically acceptable salts thereof, process comprising hydrolysing a thienopyridinonecarboxylic ester of formula:

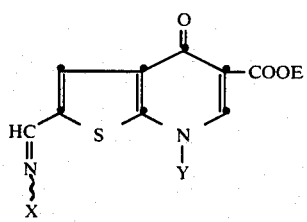

in which X and Y are as defined above and E represents a lower alkyl radical and, when X is hydroxy, submitting if required, the product so obtained to an acylating reaction with a lower alkanoyl halide and optionally transforming the hydrolysis and acylation product into pharmaceutically acceptable salts.

The hydrolysis can be conducted in accordance with known saponifying procedures by treatment under reflux with a mineral base such as sodium or potassium hydroxide followed by acidification with a mineral acid such as hydrochloric acid.

Where, in the compound of formula II the substituent X represents the group:

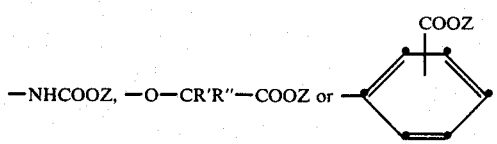

in which R' and R" are as defined above and Z represents a lower alkyl radical the operation of saponification can be conducted avoiding the saponification of the group COOZ. For this purpose, use may be made, for example, of one single equivalent of base per equivalent of ester of formula II at about 0° C. However an easily hydrolysable thienopyridinonecarboxylic ester of formula II above is preferably used as starting product so that hydrolysis occurs without affecting the group COOZ. For this purpose, a very valuable group E is the tert-butyl group which is easily split by the action of trifluoroacetic acid.

In this case, hydrolysis can be conducted at room-temperature using the same trifluoroacetic acid as solvent for the reaction.

The compound of formula I obtained after hydrolysis can be transformed into pharmaceutically acceptable salts in accordance with known procedures. When X represents a group:

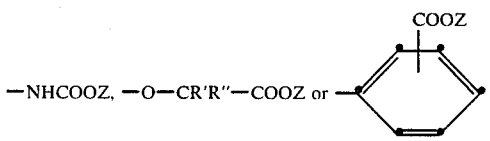

in which Z is hydrogen, the salification can be carried out simultaneously on both carboxy groups.

To prepare a compound of formula I in which X represents a lower alkanoyloxy group, the product resulting from the hydrolysis of the compound of formula II in which X is hydroxy is submitted as hereabove indicated to an acylating reaction, in accordance with known procedures with an alkanoyl halide preferably the chloride or the bromide.

The compounds of formula II used as starting compounds are prepared from the corresponding aldehydes of formula:

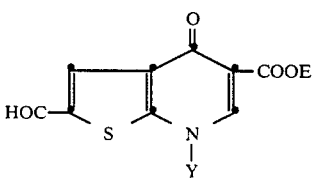

in which Y and E are as defined above.

To prepare the compounds of formula II in which X is a hydroxy group, the thienopyridinone of formula III is treated with hydroxylamine hydrochloride at room-temperature in an organic solvent such as ethanol.

To prepare the compounds of formula II in which X is a group —O—C(R'R")—W or a lower alkoxy group non substituted or substituted by a hydroxy, lower alkoxy, di-(lower alkyl)-amino, piperidino, pyrrolidino, morpholino or N-(lower alkyl)-piperazino group, the compounds of formula II in which X is hydroxy are treated with a lower alkyl chloride, bromide or iodide in which the alkyl radical is unsubstituted or substituted as indicated above or with a halide of formula Hal—C—(R'R")—W in which Hal is chlorine, bromine or iodine and R', R" and W are as defined above, in the presence of a basic agent such as sodium or potassium carbonate or sodium or potassium bicarbonate.

To prepare the compounds of formula II in which X represents a group:

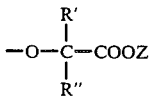

in which R' and R" are as defined above and Z represents a lower alkyl radical, the compounds of formula II in which X is hydroxy are treated with a compound of formula:

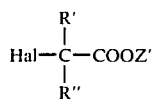

wherein Hal is chlorine, bromine or iodine, R' and R" are as defined above and Z' is a lower alkyl, in the presence of a base such as sodium or potassium carbonate, sodium or potassium hydroxide or triethylamine.

The product so obtained can be hydrolysed in accordance with classical procedures. Nevertheless, when saponification is undertaken, the splitting of both substituents Z' and E occurs at the same time as the formation of compounds of formula I in which X represents a group:

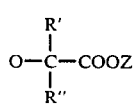

in which Z is hydrogen.

Therefore, to prepare the compounds of formula II in which X represents a group:

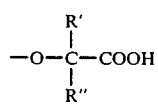

as defined above, the saponification is undertaken under mild conditions to avoid saponifying the group COOE. If the group Z' is suitably chosen, hydrolysis can be effected in a selective manner. For this purpose, a very convenient Z' group is the tert-butyl group which is easily split by the action of trifluoroacetic acid.

To prepare the compounds of formula II in which X represents a group:

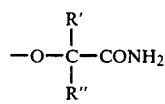

in which R' and R" are as defined above, the corresponding compounds of formula II in which X represents a group:

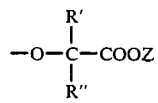

wherein R' and R" are as defined above and Z is hydrogen, the said compounds having been prepared as above described, are transformed into their functional derivatives on the free carboxylic acid radical and the functional derivatives so obtained are treated with gaseous ammonia.

As a functional derivative, there can be used a mixed anhydride such as that formed in situ by the action of isobutyl chloroformiate, an active ester such as p-nitrophenyl ester or the symetric anhydride formed by the action of a carbodiimide such as cyclohexylcarbodiimide.

To prepare the compounds of formula II in which X represents a group:

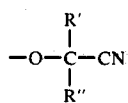

in which R' and R" are as defined above, a compound of formula II in which X is hydroxy is treated with a compound of formula:

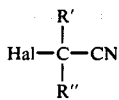

in which R' and R" are as defined above and Hal is chlorine, bromine or iodine, in the presence of a base such as sodium or potassium carbonate, sodium or potassium hydroxide or triethylamine.

To prepare the compounds of formula II in which X represents a phenyl radical unsubstituted or substituted by an atom of fluorine, chlorine, bromine or iodine or by a hydroxy, lower alkoxy or nitro group, the thienopyridinone of formula III is refluxed with aniline or an aniline of which the phenyl radical is substituted as indicated above.

To prepare the compounds of formula II in which X represents a group:

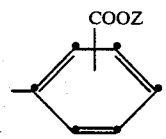

wherein Z is as defined above, the thienopyridinone of formula III is treated under reflux with an aniline of formula:

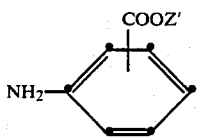

in which Z' is as defined above.

The product so obtained can be hydrolised in accordance with classical procedures. Nevertheless, when saponification is undertaken, the splitting of both substituents Z' and E occurs at the same time as the formation of compounds of formula I in which X represents a group:

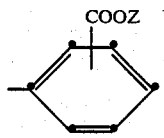

wherein Z is hydrogen.

Therefore, to prepare the compounds of formula II in which X represents a group:

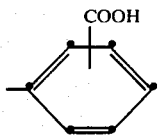

the saponification is undertaken under mild conditions to avoid saponifying the group COOE. If the group Z' is suitably chosen, hydrolysis can be effected in a selective manner. For this purpose, a very convenient group is the tert-butyl group which is easily split by the action of trifluoroacetic acid.

To prepare the compounds of formula II in which X represents an amino or a lower alkylamino group, the thienopyridinone of formula III is treated with hydrazine or a lower alkylhydrazine in the presence of a base, for instance sodium or potassium hydroxide.

To prepare the compounds of formula II in which X represents a group:

—NH—COOZ wherein Z is a defined above, the thienopyridinone of formula III is treated in the presence of a base as defined above with a lower alkyl carbazate of general formula:

NH₂—NH—COOZ' in which Z' is as defined above.

The product so obtained can be hydrolysed in accordance with classical procedures. Nevertheless, when saponification is undertaken, the splitting of both substituents Z' and E occurs at the same time as the formation of compounds of formula I in which X represents a group:

—NH—COOZ wherein Z is hydrogen.

Therefore, to prepare the compounds of formula II in which X represents a group:

—NH—COOH the saponification is undertaken under mild conditions to avoid saponifying the group COOE. If the group Z' is suitably chosen, hydrolysis can be effected in a selective manner. For this purpose, a very convenient group is the tert-butyl group which is easily split by the action of trifluoroacetic acid.

As an alternative procedure, the compounds of formula I in which X represents a hydroxy, amino, lower alkylamino, lower alkoxy or lower alkanoyloxy group as defined in formula I or a group of formula:

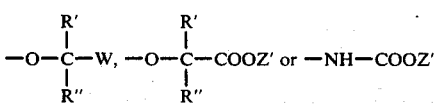

in which R', R", W and Z' are as defined above, can be obtained first by hydrolysing the compounds of formula III, in accordance with classical saponification procedures, by heating under reflux in a basic medium for example in the presence of sodium or potassium hydroxide, then acidifying with a mineral acid such as hydrochloric acid to obtain an aldehyde.

The aldehyde so obtained of general formula:

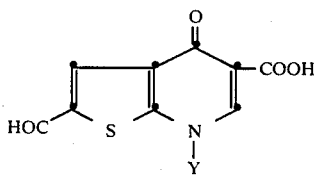
IV in which Y is as defined above, is then treated, in the presence of a base, for instance sodium or potassium hydroxide, with hydroxylamine, hydrazine, a lower alkylhydrazine, a lower alkyloxyamine, a lower alkanoyloxyamine or a compound of general formula:

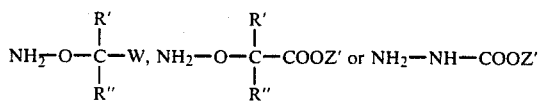

in accordance with the method described above, and subsequently acidified with a mineral acid for instance hydrochloric acid. The acid so obtained is then, if desired, transformed into a pharmaceutically acceptable salt.

The processes described above, taken as a whole, enable the compounds of formula I to be prepared in the form of mixtures of syn- and anti-isomers. These isomers can be obtained individually by classical procedures, for instance by separating them from their mixtures for example by chromatography, fractional crystallisation, etc.

In accordance with another procedure, the individual syn- and anti-isomers of the compounds of formula I can be prepared by hydrolysing the corresponding individual syn- and anti-isomers of formula II using the method above described for the preparation of mixtures of isomers of formula I.

The compounds III and IV are novel and useful as intermediates.

Thus, another object of the invention relates to compounds of formula:

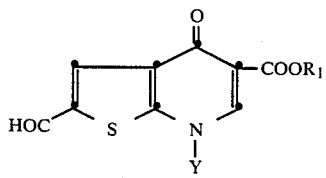
V in which Y and R₁, which are the same or different, each represent hydrogen or a lower alkyl radical.

The compounds of formula V are prepared, in accordance with another aspect of the invention, from the thiophene derivatives of formula:

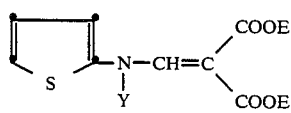
VI in which Y and E are as described above, which are reacted with phosphorous oxychloride and N-methylformanilide to obtain an aldehyde of formula:

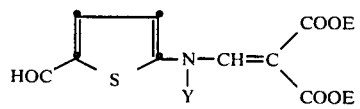
VII in which Y and E are as defined above.

A thermic cyclisation of the aldehyde of formula VII is then undertaken in the presence of polyphosphoric acid to obtain, after decomposition, the aldehydes of formula III which can, if required, be saponified as described above.

The compounds of formula VI can be obtained, when Y represents hydrogen, in accordance with the method described in Eur. J. Med. Chem. 1978, 13(3), 265–269. The compound of formula VI, in which Y is hydrogen and E is ethyl, is described in the cited publication.

When, in formula VI, Y represents a lower alkyl, the products concerned can be prepared by reacting an diethyl (2-thienyl)-aminomethylenemalonate with a lower alkyl p-toluenesulphonate in the presence of an alkali metal carbonate.

The compounds of formula VII above are novel and represent another object of the present invention.

Numerous compounds are already known and used as antibacterial agents. However, such compounds are not always advantageous as regards efficacy, antibacterial spectrum and toxicity.

The search for novel bactericidal compounds is, therefore, of paramount importance.

Thienopyridinone derivatives are already known which are endowed with bactericidal properties. Such derivatives have been described in Belgian Pat. No. 858,479 which more specifically relates to 7-alkyl-2-carboxy-4,7-dihydro-4-oxo-thieno[2,3-b]pyridine-5-carboxylic acids. Bactericidal thienopyridinone derivatives are also cited in Japanese patent application No. 51-100092 which describes more particularly 7-alkyl-4,7-dihydro-4-oxo-thieno[2,3-b]pyridine-5-carboxylic acids substituted in the 2-position by a nitro radical.

It has now been found, in accordance with the invention, that fixing a substituted or unsubstituted imino, oxyimino or hydrazono group in the 2-position of 7-alkyl-4,7-dihydro-4-oxo-thieno[2,3-b]pyridine-5-carboxylic acids provides compounds presenting very useful bactericidal properties. These properties, have even been found to be superior to those presented by known 7-alkyl-4,7-dihydro-4-oxo-thieno[2,3-b]pyridine-5-carboxylic acids and in particular 7-alkyl-2-carboxy- or 2-nitro-4,7-dihydro-4-oxo-thieno[2,3-b]pyridine-5-carboxylic acids.

It has been found that compounds of formula I above and pharmaceutically acceptable salts thereof possess marked bactericidal properties against a large number of pathogenic strains namely gram-positive and gram-negative bacteria as well as against other micro-organisms.

Furthermore, the level of toxicity presented by the compounds of the invention is not such as to hinder their therapeutic use.

In this respect, the compounds of the invention may be used at the daily dose of 10 to 100 mg/kg against bacterial infections in mammals caused by, for instance, Escherichia coli, Proteus, Klebsiella, Salmonella, Shigella, Serratia or Enterobacter.

Thus another aspect of the invention relates to pharmaceutical compositions, more particularly for the treatment of bacterial infections containing as active principle, a compound of formula I above or a pharmaceutically acceptable salt thereof.

Tests carried out in vitro in accordance with the experimental procedure described hereunder have provided evidence of the antibacterial activity in question.

For this purpose, the M.I.C. were determined i.e. the minimal inhibiting concentrations of the compound under study acting on the growth of the bacteria at 37° C.

The serial dilutions method was used utilizing a MUELLER HINTON gelose medium at pH=7.4 and a bacterial inoculum of $10^4$ units forming colonies. This inoculum was applied to the gelose by means of a multiple sowing device.

A scale of concentrations ranging from 100 to 0.05 μg/ml of compound to be studied was used starting from mother solutions titrating 1000 μg/ml, all the subsequent dilutions being effected in distilled water.

The results obtained with the following compounds of the invention are given hereunder:

4,7-Dihydro-7-ethyl-2-hydroxyiminomethyl-4-oxo-thieno[2,3-b]pyridine-5-carboxylic acid (Compound A)

4,7-Dihydro-7-ethyl-2-hydroxyiminomethyl-4-oxo-thieno[2,3-b]pyridine-5-carboxylic acid, anti-isomer (Compound B)

4,7-Dihydro-7-ethyl-2-hydroxyiminomethyl-4-oxo-thieno[2,3-b]pyridine-5-carboxylic acid, syn-isomer (Compound C)

4,7-Dihydro-7-ethyl-2-methoxyiminomethyl-4-oxo-thieno[2,3-b]pyridine-5-carboxylic acid (Compound D)

4,7-Dihydro-7-ethyl-2-(3-N,N-dimethylamino-propoxy)-iminomethyl-4-oxo-thieno[2,3-b]pyridine-5-carboxylic acid (Compound E)

4,7-Dihydro-7-ethyl-2-N-(2-hydroxy-phenyl)-iminomethyl-4-oxo-thieno[2,3-b]pyridine-5-carboxylic acid (Compound F)

4,7-Dihydro-7-ethyl-2-N-(4-methoxy-phenyl)-iminomethyl-4-oxo-thieno[2,3-b]pyridine-5-carboxylic acid (Compound G)

4,7-Dihydro-7-ethyl-2-methoxyiminomethyl-4-oxo-thieno[2,3-b]pyridine-5-carboxylic acid, anti-isomer (Compound H)

4,7-Dihydro-7-ethyl-4-oxo-2-tert-butoxyiminomethyl-thieno[2,3-b]pyridine-5-carboxylic acid (Compound I)

4,7-Dihydro-7-ethyl-2-N-phenyl-iminomethyl-4-oxo-thieno[2,3-b]pyridine-5-carboxylic acid (Compound J)

For comparison purposes, similar tests were carried out with two known thienopyridinone derivatives namely 4,7-dihydro-7-ethyl-2-carboxy-4-oxo-thieno[2,3-b]pyridine-5-carboxylic acid (Compound X) and 4,7-dihydro-7-ethyl-2-nitro-4-oxo-thieno[2,3-b]pyridine-5-carboxylic acid (Compound Y).

see following table

These results show that the compounds of the invention are superior to the known compounds.

It will be appreciated that for therapeutic use the compounds of the invention will normally be administered in the form of a pharmaceutical composition, which may be in a dosage unit form appropriate to the desired mode of administration.

Thus, the pharmaceutical composition may be in a dosage unit form suitable for oral administration, for example, a coated or uncoated tablet, a hard- or soft-gelatin capsule, a packaged powder, a suspension or a syrup. The composition may alternatively take the form of a suppository for rectal administration, a sterile solution or suspension for parenteral administration or a form suitable for intra-uterine or intra-mammary administration.

When in dosage form, the composition may contain from 100 to 5000 mg of active ingredient per dosage unit form the said active ingredient being alone or in a mixture with appropriate pharmaceutical carriers or excipients such as for example distilled water, starches, talc, magnesium stearate, polyvinylpyrrolidone, alginic acid, colloidal silica, sodium chloride, titane dioxide, cocoa butter, flavouring agents and the like.

The following non-limitative Examples illustrate the invention.

PREPARATIONS (a) Diethyl N-ethyl-N-(2-thienyl)-aminoethylenemalonate

In 150 ml of acetone were dissolved 18 g (0.067 mol) of diethyl(2-thienyl)-aminomethylenemalonate and 11 g (0.08 mol) of potassium carbonate. The medium was heated under reflux for 3 hours and the precipitate which formed was filtered out. After washing with ethyl ether, the solid was dried and then dissolved in a solution of 150 ml of N,N-dimethylformamide containing 13 g (0.066 mol) of ethyl p-toluenesulfonate. The mixture was refluxed for 10 hours.

TABLE

| | MIC (μg/ml) COMPOUNDS | | | | | | | | | | |
|---|---|---|---|---|---|---|---|---|---|---|---|
| Strains | A | B | C | D | E | F | G | H | I | J | X | Y |
| *Staphylococcus aureus* 53154 IP | 25 | 12.5 | 12.5 | 1.56 | 6.25 | 100 | >100 | >50 | >50 | >100 | >100 | >100 |
| *Streptococcus faecalis* 5855 IP | >100 | >100 | >100 | >100 | 100 | >100 | >100 | >100 | >100 | >100 | >100 | >100 |
| *Bacillus subtilis* ATCC 6633 | — | 6.25 | 6.25 | 0.78 | 6.25 | 6.25 | 6.25 | 0.8 | 1.56 | — | — | — |
| *Escherichia coli* 54127 IP | 3.12 | 3.12 | 12.5 | 0.78 | 6.25 | 1.56 | 1.56 | 1.56 | >25 | 3.12 | >100 | 3.12 |
| *Escherichia coli* SOL RL 90 | 6.25 | 3.12 | 3.12 | 3.12 | 25 | 3.12 | 3.12 | 6.25 | >50 | 6.25 | >100 | 6.25 |
| *Citrobacter freundii* GN 346 | 6.25 | 3.12 | 3.12 | 3.12 | 12.5 | 6.25 | 6.25 | 6.25 | >25 | 12.5 | >100 | 12.5 |
| *Proteus vulgaris* RL 99 bis | 1.56 | 0.80 | 12.5 | 0.78 | 12.5 | 3.12 | 1.56 | 1.56 | >50 | 3.12 | >100 | 3.12 |
| *Proteus mirabilis* ATCC 21100 | 1.56 | 1.56 | 12.5 | 0.78 | 3.12 | 3.12 | 6.25 | 0.8 | >25 | 12.5 | >100 | 12.5 |
| *Proteus morganii* 1510 | 1.56 | 0.40 | 0.40 | 3.12 | 25 | 6.25 | 0.78 | 0.8 | >25 | 3.12 | >100 | 3.12 |
| *Providencia stuartii* 5158 | 6.25 | 6.25 | 12.5 | 3.12 | 25 | 12.5 | 12.5 | 6.25 | >50 | 12.5 | >100 | 12.5 |
| *Serratia liquefaciens* 376 | 100 | 50 | 50 | 50 | 50 | >100 | 100 | >25 | >25 | >100 | >100 | >100 |
| *Klebsiella pneumoniae* ATCC 10031 | 1.56 | 1.56 | 12.5 | 0.2 | 3.12 | 12.5 | 12.5 | 0.4 | 3.12 | 50 | >100 | 50 |
| *Klebsiella pneumoniae* R 30 | 6.25 | 6.25 | 6.25 | 3.12 | 25 | 12.5 | 12.5 | 6.25 | >25 | 25 | >100 | 25 |

TABLE-continued

| Strains | MIC (μg/ml) COMPOUNDS | | | | | | | | | | |
|---|---|---|---|---|---|---|---|---|---|---|---|
| | A | B | C | D | E | F | G | H | I | J | X | Y |
| *Enterobacter cloacae* P 99 | 6.25 | 6.25 | 3.12 | 1.56 | 12.5 | 6.25 | 6.25 | 3.12 | >25 | 50 | >100 | 50 |
| *Enterobacter hafniae* RO 46 | 1.56 | 3.12 | 12.5 | 1.56 | 6.25 | 1.56 | 1.56 | 3.12 | >25 | 3.12 | >100 | 3.12 |
| *Shigella sonnei* R 018 | 1.56 | 0.80 | 0.80 | 1.56 | 25 | 6.25 | 6.25 | 3.12 | >50 | 3.12 | >100 | 3.12 |
| *Salmonella typhimurium* A 222 IP | 6.25 | 3.12 | 3.12 | 3.12 | 25 | 3.12 | 3.12 | 12.5 | >50 | 6.25 | >100 | 6.25 |
| *Salmonella typhi* ATCC 6539 | 6.25 | 6.25 | 3.12 | 3.12 | 25 | 3.12 | 6.25 | 25 | >25 | 25 | >100 | 25 |
| *Bordetella bronchiseptica* ATCC 4617 | >100 | >100 | >100 | 12.5 | >100 | >100 | >100 | >25 | >25 | >100 | >100 | >100 |
| *Pseudomonas aeruginosa* 8203 | 50 | 100 | >100 | >100 | >100 | >100 | >100 | >25 | >25 | >100 | >100 | >100 |
| *Acinetobacter calcoaceticus* C 1733 | >100 | >100 | >100 | >100 | >100 | 100 | >100 | >25 | >25 | >100 | >100 | >100 |

After cooling, the solvent was eliminated under reduced pressure. The residue was taken up in chloroform, washed with water and dried. The organic phase was evaporated to dryness and the residue was dissolved in warm hexane. After precipitating when cool, the precipitate obtained was suction-filtered on sintered glass.

In this manner, diethyl N-ethyl-N-(2-thienyl)-aminomethylenemalonate was obtained with a yield of 80%. M.P.: 41°–42° C. Thin layer chromatography $$\begin{cases} CH_2Cl_2: 6 \text{ Rf: } 0.8 \\ \text{ether: } 4 \end{cases}$$

(b) Diethyl N-ethyl-N-(5-formyl-2-thienyl)-aminomethylenemalonate

To the VILSMEIR reagent (N-methylformanilide and phosphorous oxychloride), were slowly added, while stirring, .5 g of diethyl N-ethyl-N-(2-thienyl)-aminomethylenemalonate dissolved in 20 ml of 1,2-dichloro-ethane. Stirring was maintained for 5 hours after which the reaction mixture was poured into 100 g of ice containing 5 g of sodium acetate to neutralise the solution. The aldehyde was extracted and the organic phase was washed with water, dried and evaporated to dryness. The residue was taken up in warm hexane and the precipitate was filtered out on sintered glass.

In this manner, diethyl N-ethyl-N-(5-formyl-2-thienyl)-aminomethylenemalonate was obtained in a yield of 70%. M.P.: 45° C. (hexane)

EXAMPLE I 4,7-Dihydro-7-ethyl-2-formyl-4-oxo-thieno[2,3-b]pyridine-5-carboxylic acid ethyl ester.

While stirring, 20 g of polyphosphoric acid were heated and 1.5 g of diethyl N-ethyl-N-(5-formyl-2-thienyl)-aminoethylenemalonate added. Stirring and heating were maintained for 30 min. After cooling to room-temperature, the medium was decomposed by adding 100 g of crushed ice. After homogeneisating, the cooled solution was brought to pH 3–4 by adding sodium carbonate and then extracted with chloroform. The organic phase was washed with water, dried and evaporated to dryness.

In this manner, 1 g of 4,7-dihydro-7-ethyl-2-formyl-4-oxo-thieno[2,3-b]pyridine-5-carboxylic acid ethyl ester was obtained in a yield of 78%. M.P.: 205° C. (ethanol)

EXAMPLE II 4,7-Dihydro-7-ethyl-2-formyl-4-oxo-thieno[2,3-b]pyridine-5-carboxylic acid In a water-bath, there was heated for several minutes a mixture of 3 parts of ethyl 4,7-dihydro-7-ethyl-2-formyl-4-oxo-thieno[2,3-b]pyridine-5-carboxylate and 100 parts by volume of a 10%-potassium hydroxide solution in ethanol. The mixture was allowed to stand for 6 hours at room-temperature. The precipitate was filtered out, washed with ethanol and diluted hydrochloric acid was added.

In this manner, 4,7-dihydro-7-ethyl-2-formyl-4-oxo-thieno[2,3-b]pyridine-5-carboxylic acid was obtained.

EXAMPLE III 4,7-Dihydro-7-ethyl-2-hydroxyiminomethyl-4-oxo-thieno[2,3-b]pyridine-5-carboxylic acid ethyl ester.

In 50 ml of warm ethanol was dissolved 0.5 g of 4,7-dihydro-7-ethyl-2-formyl-4-oxo-thieno[2,3-b]pyridine-5-carboxylic acid ethyl ester. The solution was cooled to room-temperature, then 0.2 g of hydroxylamine hydrochloride was added followed by 2 ml of a 5%-solution of sodium hydroxide. After filtration, 4,7-dihydro-7-ethyl-2-hydroxyiminomethyl-4-oxo-thieno[2,3-b]pyridine-5-carboxylic acid ethyl ester was obtained in a yield of 80%.

EXAMPLE IV 4,7-Dihydro-7-ethyl-2-hydroxyiminomethyl-4-oxo-thieno[2,3-b]pyridine-5-carboxylic acid ethyl ester.

In 50 ml of warm ethanol was dissolved 0.8 g (2.8 mmol) of 4,7-dihydro-7-ethyl-2-formyl-4-oxo-thieno[2,3-b]pyridine-5-carboxylic acid ethyl ester.

After cooling of the solution to room-temperature there was added 0.25 g (3.6 mmol) of hydroxylamine hydrochloride dissolved in 1 ml of water. To this solution, a solution of diluted sodium hydroxide was added to obtain a pH of about 7. Stirring was maintained for 2 hours at room-temperature. The reaction mixture was placed in a refrigerator to provoke the precipitation of the ethyl ester of 4,7-dihydro-7-ethyl-2-hydroxyiminomethyl-4-oxo-thieno[2,3-b]pyridine-5-carboxylic acid which was then filtered out. Yield: 70%

A thin layer chromatography on silica gel (eluent: chloroform/ethanol 18:2) showed 2 spots: Rf=0.43 and Rf=0.36.

The two isomers obtained were separated out by recrystallisation from a N,N-dimethylformamide/methanol mixture.

The compound with a Rf=0.43 was in crystal form in N,N-dimethylformamide at room-temperature, the compound with a Rf=0.36 was in crystal form in cool methanol.

The study of the NMR spectra showed that the isomer with a Rf=0.43 was the anti-isomer and that with the Rf=0.36 was the syn-isomer.

Anti-iosmer

M.P.: 228-290° C. (decomposition)
N.M.R.

| 1.25 ppm | triplet | | |
| 1.4 ppm | triplet | | |
| 4.2 ppm | quartet | | |
| 7.65 ppm | singlet | CH | $H_3$ |
| 8.5 ppm | singlet | CH | oxime |
| 8.6 ppm | singlet | CH | $H_6$ |

Syn-isomer

M.P.: 315-318° C.
N.M.R.

| 7.8 ppm | singlet | CH | oxime |

EXAMPLE V 4,7-Dihydro-7-ethyl-2-carbomethoxyiminomethyl-4-oxo-thieno[2,3-b]pyridine-5-carboxylic acid ethyl ester In 40 ml of warm ethanol was dissolved 0.3 g (1.1 mmol) of 4,7-dihydro-7-ethyl-2-formyl-4-oxo-thieno[2,3-b]pyridine-5-carboxylic acid ethyl ester. The solution was cooled to 20° C. and 0.14 g (1.1 mmol) of carboxymethoxyamine dissolved in 10 ml of water was added. The reaction mixture was maintained under stirring for 1 hour at room-temperature and the evolution of the reaction was monitored by thin layer chromatography (eluent: chloroform/ethanol 19:1).

In this manner, a solution containing 4,7-dihydro-7-ethyl-2-carbomethoxyiminomethyl-4-oxo-thieno[2,3-b]pyridine-5-carboxylic acid ethyl ester was obtained.

EXAMPLE VI 4,7-Dihydro-7-ethyl-2-(4-methoxy-phenyl)-iminomethyl-4-oxo-thieno[2,3-b]pyridine-5-carboxylic acid ethyl ester.

At the reflux temperature of methanol, there was heated for 3 hours a mixture of 0.2 g (0.72 mmol) of 4,7-dihydro-7-ethyl-2-formyl-4-oxo-thieno[2,3-b]pyridine-5-carboxylic acid ethyl ester and 0.09 g (0.72 mmol) of p-methoxy-aniline in 20 ml of methanol. After cooling of the reaction mixture, the desired imine was collected by filtration with a yield of 50%.

Thin layer chromatography: Rf=0.28 (eluent: chloroform/ethanol 19:1).

Starting from intermediate products as hereabove prepared, the following compounds of formula I were obtained:

EXAMPLE 1

4,7-Dihydro-7-ethyl-2-hydroxyiminomethyl-4-oxo-thieno[2,3-b]pyridine-5-carboxylic acid.

For 1 hour, 1 g of 4,7-dihydro-7-ethyl-2-hydroxyiminomethyl-4-oxo-thieno[2,3-b]pyridine-5-carboxylic acid ethyl ester was refluxed in 30 ml of 10%-sodium hydroxide. After cooling, the solution was filtered and acidified with 10%-hydrochloric acid. After filtration 4,7-dihydro-7-ethyl-2-hydroxyiminomethyl-4-oxo-thieno[2,3-b]pyridine-5-carboxylic acid was obtained in a yield of 80%. M.P.: 315°-317° C. (N,N-dimethylformamide).

EXAMPLE 2

4,7-Dihydro-7-ethyl-2-hydroxyiminomethyl-4-oxo-thieno[2,3-b]pyridine carboxylic acid, anti-isomer.

In 10 ml of water containing 0.4 g of sodium hydroxide was dissolved 0.125 g (0.42 mmol) of 4,7-dihydro-7-ethyl-2-hydroxyiminomethyl-4-oxo-thieno[2,3-b]pyridine-5-carboxylic acid ethyl ester, anti-isomer. The solution obtained was maintained under stirring at room-temperature for 1 hour and then acidified with concentrated hydrochloric acid. The precipitate obtained was filtered out, washed with water and then with alcohol. After drying, 4,7-dihydro-7-ethyl-2-hydroiminomethyl-4-oxo-thieno[2,3-b]pyridine-5-carboxylic acid, anti-isomer was obtained in a yield of 98%.

M.P.: 322°-334° C. N.M.R. Spectrum

The N.M.R. spectrum shows that no isomerisation occurred during the reaction

| 1.5 ppm | triplet | $CH_3$ | |
| 4.4 ppm | quartet | $CH_2$ | |
| 7.7 ppm | singlet | CH | $H_3$ |
| 8.5 ppm | singlet | CH | oxime |
| 8.9 ppm | singlet | CH | $H_6$ |

EXAMPLE 3

4,7-Dihydro-7-ethyl-2-hydroxyiminomethyl-4-oxo-thieno[2,3-b]pyridine-5-carboxylic acid, syn-isomer The same procedure as that described in Example 2 provided, from 4,7-dihydro-7-ethyl-2-hydroxyiminomethyl-4-oxo-thieno[2,3-b]pyridine-5-carboxylic acid ethyl ester, syn-isomer, 4,7-dihydro-7-ethyl-2-hydroxyimino-4-oxo-thieno[2,3-b]pyridine-5-carboxylic acid, syn-isomer in a yield of 58%.

M.P.: 330°-335° C. N.M.R. Spectrum

Examination of the N.M.R. spectrum shows that no isomerisation occurred during the reaction.

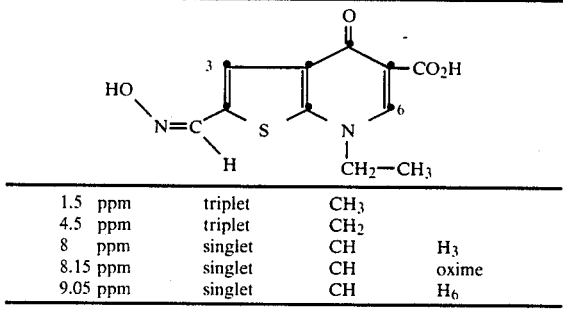

| 1.5 ppm | triplet | CH₃ | |
| --- | --- | --- | --- |
| 4.5 ppm | triplet | CH₂ | |
| 8 ppm | singlet | CH | H₃ |
| 8.15 ppm | singlet | CH | oxime |
| 9.05 ppm | singlet | CH | H₆ |

EXAMPLE 4

4,7-Dihydro-7-ethyl-2-carboxymethoxyiminomethyl-4-oxo-thieno[2,3-b]pyridine-5-carboxylic acid.

To the solution obtained in Example V containing 4,7-dihydro-7-ethyl-2-carbomethoxyiminomethyl-4-oxo-thieno[2,3-b]pyridine-5-carboxylic acid ethyl ester was added 0.15 g (3.7 mmols) of sodium hydroxide in 5 ml of water. The medium was maintained under stirring for 3 hours at room-temperature. The precipitate formed was filtered out, washed with ethanol and then with ethyl ether. The product so obtained was then taken up in 200 ml of water and the solution was acidified with concentrated hydrochloric acid. The precipitate so formed was filtered out, washed with water and then with ethanol. After drying, 4,7-dihydro-7-ethyl-2-carboxymethoxyiminomethyl-4-oxo-thieno[2,3-b]pyridine-5-carboxylic acid was obtained in a yield of 40%.

M.P.: 249°–250° C. (N,N-dimethylformamide/ethanol). Thin layer chromatography (silica gel): Rf=0.57 (eluent: chloroform/ethanol/water 10:9.5:0.5).

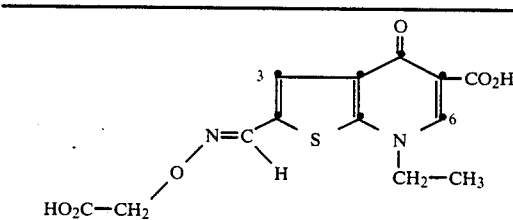

I.R. Spectrum
Conforms
N.M.R. Spectrum (DMSO d₆)

| 1.5 ppm | triplet | CH₃ | | |
| --- | --- | --- | --- | --- |
| 4.5 ppm | quartet | CH₂ | | |
| 4.7 ppm | singlet | CH₂ | | (anti-isomer) |
| 4.85 ppm | singlet | CH₂ | | (syn-isomer) |
| 7.9 ppm | singlet | CH | H₃ | |
| 8.7 ppm | singlet | CH | oxime | anti-isomer |
| 9.0 ppm | singlet | CH | H₆ | |

EXAMPLE 5

4,7-Dihydro-7-ethyl-2-(4-methoxy-phenyl)-iminomethyl-4-oxo-thieno[2,3-b]pyridine-5-carboxylic acid.

In 10 ml of water containing 0.1 g of sodium hydroxide and 10 ml of ethanol was dissolved 0.1 g of the 4,7-dihydro-7-ethyl-2-(4-methoxy-phenyl)-iminomethyl-4-oxo-thieno[2,3-b]pyridine-5-carboxylic acid ethyl ester obtained in Example VI. The mixture was stirred at room-temperature to total hydrolysis and the progress of the reaction was monitored by thin layer chromatography (eluent: chloroform/ethanol 19:1).

When the reaction was terminated, the solution was neutralised by adding a solution of diluted hydrochloric acid. The precipitate so formed was suction-filtered on sintered glass and washed first with water and then with ethanol.

After drying in a dessicator, 0.08 g of 4,7-dihydro-7-ethyl-2-(4-methoxy-phenyl)-iminomethyl-4-oxo-thieno[2,3-b]pyridine-5-carboxylic acid was collected in a yield of 90%.

M.P.: 301°–303° C. (N,N-dimethylformamide)

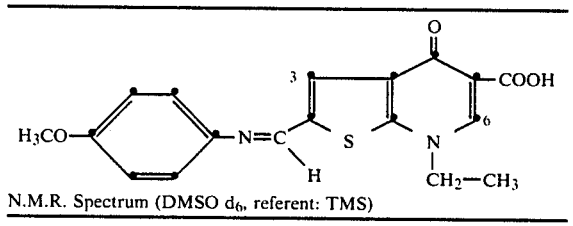

N.M.R. Spectrum (DMSO d₆, referent: TMS)

| 1.8 ppm | triplet | 3H | |
| --- | --- | --- | --- |
| 4.0 ppm | singlet | 3H | |
| 4.7 ppm | quartet | 2H | |
| 7.4 ppm | group (4 peaks) | 4H | |
| 8.3 ppm | singlet | 1H | (H₃) } anti-isomer |
| 9.2 ppm | singlet | 2H | (H₆ and imine) |

EXAMPLE 6

4,7-Dihydro-7-ethyl-4-oxo-2-tert-butoxyiminomethyl-thieno[2,3-b]pyridine-5-carboxylic acid.

In 40 ml of water containing 0.1 g (2.5 mmols) of sodium hydroxide was dissolved 0.4 g (1.6 mmol) of the 4,7-dihydro-7-ethyl-2-formyl-4-oxo-thieno[2,3-b]pyridine-5-carboxylic acid obtained in Example II. When the solution was clear, 0.2 g (1.6 mmol) of tert-butoxyamine hydrochloride dissolved in 5 ml of water was added and the resulting solution was maintained under stirring for 2 hours. The medium was neutralised with diluted hydrochloric acid and the precipitate which formed was suction-filtered on sintered glass. This precipitate was washed first with water and then with ethanol. After drying in a dessicator, 0.4 g of 4,7-dihydro-7-ethyl-4-oxo-2-tert-butoxyiminomethyl-thieno[2,3-b]pyridine-5-carboxylic acid in a yield of 80%.

M.P.: 223°–224° C. (N,N-dimethylformamide)

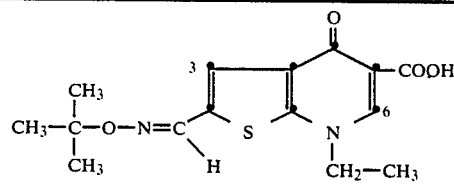

N.M.R. Spectrum (DMSO d₆, referent TMS)
The product contained 70% of the anti-isomer and 30% of the syn-isomer.

| 1.4 ppm | singlet | (CH₃)₃ | | anti-isomer |
| --- | --- | --- | --- | --- |
| 1.5 ppm | singlet | (CH₃)₃ | | syn-isomer |
| 1.8 ppm | triplet | CH₃ | | |
| 4.5 ppm | quartet | CH₂ | | |
| 7.9 ppm | singlet | H₃ | | anti-isomer |
| 8.1 ppm | singlet | H₃ | | syn-isomer |
| 8.25 ppm | singlet | H | oxime | syn-isomer |
| 8.6 ppm | singlet | H | oxime | anti-isomer |

-continued

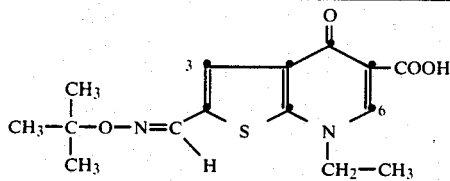

N.M.R. Spectrum (DMSO d$_6$, referent TMS)
The product contained 70% of the anti-isomer and
30% of the syn-isomer.

| 9.05 ppm | singlet | H$_6$ | anti-isomer |
|---|---|---|---|
| 9.1 ppm | singlet | H$_6$ | syn-isomer |

EXAMPLE 7

4,7-Dihydro-7-ethyl-2-(carboxymethoxyamino)-iminomethyl-4-oxo-thieno[2,3-b]pyridine-5-carboxylic acid.

In 50 ml of water containing 0.05 g (1.25 mmol) of sodium hydroxide was dissolved 0.2 g of 4,7-dihydro-7-ethyl-2-formyl-4-oxo-thieno[2,3-b]pyridine-5-carboxylic acid prepared as in Example II. After solubilization, 0.07 g (0.8 mmol) of methyl carbazate was added and the solution obtained was heated at 60° C. for 3 h.

The medium was cooled and then neutralised by adding diluted hydrochloric acid. The precipitate which formed was suction-filtered on sintered glass, washed with water and then with ethanol. After drying in a dessicator, 0.12 g of 4,7-dihydro-7-ethyl-2-(carboxymethoxyamino)-iminomethyl-4-oxo-thieno[2,3-b]pyridine-5-carboxylic acid was collected in the form of a pale yellow product which was recrystallised from a N,N-dimethylformamide/ethanol mixture.

M.P.: >315° C. Yield: 47%

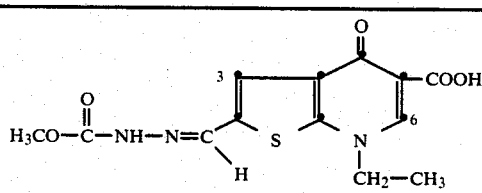

N.M.R. Spectrum (DMSO d$_6$, referent: TMS)
The product contained 100% of the anti-isomer.

| 1.5 ppm | triplet | 3H | |
|---|---|---|---|
| 3.8 ppm | singlet | 3H | |
| 4.5 ppm | quartet | 2H | |
| 7.8 ppm | singlet | H$_3$ | |
| 8.3 ppm | singlet | imine | anti-isomer |
| 8.9 ppm | singlet | H$_6$ | |

Starting from the appropriate products, the following compounds were prepared using the processes described in the foregoing Examples:

4,7-Dihydro-7-ethyl-2-methoxyiminomethyl-4-oxo-thieno[2,3-b]pyridine-5-carboxylic acid
M.P.: 244°–245° C.
4,7-Dihydro-7-ethyl-2-(3-N,N-dimethylamino-propoxy)-iminomethyl-4-oxo-thieno[2,3-b]pyridine-5-carboxylic acid
M.P.: 259°–261° C.
4,7-Dihydro-7-ethyl-2-N-(2-hydroxy-phenyl)-iminomethyl-4-oxo-thieno[2,3-b]pyridine-5-carboxylic acid
M.P.: 320°–322° C.
4,7-Dihydro-7-ethyl-2-N-phenyliminomethyl-4-oxo-thieno[2,3-b]pyridine-5-carboxylic acid
M.P.: 270°–272° C.
4,7-Dihydro-7-ethyl-2-[(1,1-dimethyl-1-carboxy)-methoxy]-iminomethyl-4-oxo-thieno[2,3-b]pyridine-5-carboxylic acid
M.P.: 218°–221° C.
4,7-Dihydro-7-ethyl-2-methoxyiminomethyl-4-oxo-thieno[2,3-b]pyridine-5-carboxylic acid, anti-isomer
M.P.: 244°–245° C.
4,7-Dihydro-7-ethyl-2-(2-N,N-diisopropylamino-ethoxy)-iminomethyl-4-oxo-thieno[2,3-b]pyridine-5-carboxylic acid
M.P.: 235°–237° C.
4,7-Dihydro-7-ethyl-2-allyloxyiminomethyl-4-oxo-thieno[2,3-b]pyridine-5-carboxylic acid
M.P.: 225°–227° C.
4,7-Dihydro-7-ethyl-2-ethoxyiminomethyl-4-oxo-thieno[2,3-b]pyridine-5-carboxylic acid
M.P.: 220°–221° C.
4,7-Dihydro-7-ethyl-2-aminoiminomethyl-4-oxo-thieno[2,3-b]pyridine-5-carboxylic acid
M.P.: >310° C.
4,7-Dihydro-7-ethyl-2-N-(4-chloro-phenyl)-iminomethyl-4-oxo-thieno[2,3-b]pyridine-5-carboxylic acid
4,7-Dihydro-7-ethyl-2-acetoxyiminomethyl-4-oxo-thieno[2,3-b]pyridine-5-carboxylic acid.
4,7-Dihydro-7-ethyl-2-hydroxymethoxyiminomethyl-4-oxo-thieno[2,3-b]pyridine-5-carboxylic acid.
4,7-Dihydro-7-ethyl-2-N-piperidinomethoxyiminomethyl-4-oxo-thieno[2,3-b]pyridine-5-carboxylic acid.
4,7-Dihydro-7-ethyl-2-ethoxymethoxyiminomethyl-4-oxo-thieno[2,3-b]pyridine-5-carboxylic acid.
4,7-Dihydro-7-ethyl-2-N-morpholinomethoxyiminomethyl-4-oxo-thieno[2,3-b]pyridine-5-carboxylic acid.
4,7-Dihydro-7-ethyl-2-N,N'-ethylpiperazinomethoxyiminomethyl-4-oxo-thieno[2,3-b]pyridine-5-carboxylic acid.
4,7-Dihydro-7-ethyl-2-N-pyrrolidinomethoxyiminomethyl-4-oxo-thieno[2,3-b]pyridine-5-carboxylic acid.
4,7-Dihydro-7-ethyl-2-propargyliminomethyl-4-oxo-thieno[2,3-b]pyridine-5-carboxylic acid.
4,7-Dihydro-7-ethyl-2-[(1,1-dimethyl-1-carbethoxy)-methoxy]-iminomethyl-4-oxo-thieno[2,3-b]pyridine-5-carboxylic acid.
4,7-Dihydro-7-ethyl-2-[(1,1-dimethyl-1-carboxy)-methoxy]-iminomethyl-4-oxo-thieno[2,3-b]pyridine-5-carboxylic acid, disodium salt.
4,7-Dihydro-7-ethyl-2-carboxymethoxyiminomethyl-4-oxo-thieno[2,3-b]pyridine-5-carboxylic acid, disodium salt.
4,7-Dihydro-7-ethyl-2-[(1,1-dimethyl-1-carbamido)-methoxy]-iminomethyl-4-oxo-thieno[2,3-b]pyridine-5-carboxylic acid.
4,7-Dihydro-7-ethyl-2-[(1,1-dimethyl-1-cyano)-methoxy]-iminomethyl-4-oxo-thieno[2,3-b]pyridine-5-carboxylic acid.
4,7-Dihydro-7-ethyl-2-(4-carbethoxy-phenyl)-iminomethyl-4-oxo-thieno[2,3-b]pyridine-5-carboxylic acid.
4,7-Dihydro-7-ethyl-2-n-ethylaminoiminomethyl-4-oxo-thieno[2,3-b]pyridine-5-carboxylic acid.

EXAMPLE 8

A sterile aqueous composition was prepared containing the following ingredients:

| | |
|---|---|
| 4,7-Dihydro-7-ethyl-2-hydroxyiminomethyl-4-oxo-thieno[2,3-b]pyridine-5-carboxylic acid | 1000 mg |
| Sodium hydroxide, water | 10 ml |
| pH of the solution: from 11 to 11.5 | |

EXAMPLE 9

4,7-Dihydro-7-ethyl-2-hydroxyiminomethyl-4-oxo-thieno[2,3-b]pyridine-5-carboxylic acid, sodium salt Into 40 ml of ethanol containing 15 ml of a 0.25N aqueous solution of sodium hydroxide was introduced 1 mmol of 4,7-dihydro-7-ethyl-2-hydroxyimino-4-oxo-thieno[2,3-b]pyridine-5-carboxylic acid. The reaction mixture was allowed to stand and the precipitate which formed was suction-filtered, washed with ethanol and dried in a dessicator.

In this manner, 4,7-dihydro-7-ethyl-2-hydroxyiminomethyl-4-oxo-thieno[2,3-b]pyridine-5-carboxylic acid, sodium salt was obtained in a yield of 85%.

We claim:

1. A thienopyridinone derivative of the formula:

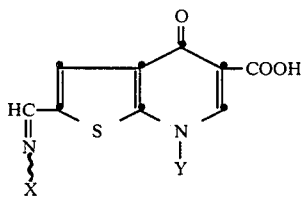

in which Y represents hydrogen or a lower alkyl group and X represents a methoxy group, and pharmaceutically acceptable salts thereof.

2. A thienopyridinone derivative according to claim 1 in which Y represents ethyl.

3. A thienopyridinone derivative according to claim 1 which is 4,7-dihydro-7-ethyl-2-methoxyiminomethyl-4-oxo-thieno[2,3-b]pyridine-5-carboxylic acid and pharmaceutically acceptable salts thereof.

4. A thienopyridinone derivative according to claim 1 which is 4,7-dihydro-7-ethyl-2-methoxyiminomethyl-4-oxo-thieno[2,3-b]pyridine-5-carboxylic acid, anti-isomer, and pharmaceutically acceptable salts thereof.

5. A thienopyridinone derivative according to claim 1 which is 4,7-dihyro-7-ethyl-2-methoxyiminomethyl-4-oxo-thieno[2,3-b]pyridine-5-carboxylic acid, syn-isomer, and pharmaceutically acceptable salts thereof.

6. An anti-bacterial pharmaceutical composition comprising, as active ingredient, from 100 to 5000 mg of a thienopyridinone derivative according to claim 1, in association with a pharmaceutical carrier or excipient.

7. A composition according to claim 6 for the treatment of bacterial infections in mammals.

8. A composition according to claim 6 in a dosage unit form.

9. A composition according to claim 7 in a dosage unit form.

10. A composition according to claim 6 wherein the thienopyridinone is 4,7-dihydro-7-ethyl-2-methoxyiminomethyl-4-oxo-thieno[2,3-b]pyridine-5-carboxylic acid.

11. A composition according to claim 7, wherein the thienopyridinone is 4,7-dihydro-7-ethyl-2-methoxyiminomethyl-4-oxo-thieno[2,3-b]pyridine-5-carboxylic acid.

12. A method for treating bacterial infections in a mammal comprising the daily administration to said mammal in need of such treatment from 10 to 100 mg/kg of a thienopyridinone derivative according to claim 1.

* * * * *